United States Patent
Schultheiss et al.

(10) Patent No.: US 7,497,835 B2
(45) Date of Patent: *Mar. 3, 2009

(54) METHOD OF TREATMENT FOR AND PREVENTION OF PERIODONTAL DISEASE

(75) Inventors: Reiner Schultheiss, Illighausen (CH); Wolfgang Schaden, Vienna (AT); John Warlick, Woodstock, GA (US)

(73) Assignee: General Patent LLC, Marietta, GA (US)

( * ) Notice: Subject to any disclaimer, the term of this patent is extended or adjusted under 35 U.S.C. 154(b) by 514 days.

This patent is subject to a terminal disclaimer.

(21) Appl. No.: 11/238,730

(22) Filed: Sep. 29, 2005

(65) Prior Publication Data

US 2006/0036194 A1    Feb. 16, 2006

Related U.S. Application Data

(63) Continuation-in-part of application No. 11/122,154, filed on May 4, 2005, now Pat. No. 7,470,240, and a continuation-in-part of application No. 11/071,156, filed on Mar. 4, 2005.

(60) Provisional application No. 60/693,143, filed on Jun. 23, 2005, provisional application No. 60/693,369, filed on Jun. 22, 2005, provisional application No. 60/642,149, filed on Jan. 10, 2005, provisional application No. 60/621,028, filed on Oct. 22, 2004.

(51) Int. Cl.
*A61H 1/02* (2006.01)

(52) U.S. Cl. .................. 601/2; 601/4; 600/437

(58) Field of Classification Search .......... 600/437; 601/2
See application file for complete search history.

(56) References Cited

U.S. PATENT DOCUMENTS 3,951,140 A    4/1976 Eggleton et al.

(Continued)

FOREIGN PATENT DOCUMENTS

DE    197 21 218 A1    11/1998

(Continued)

OTHER PUBLICATIONS

R.Meirer, et al; Extracorporal shock wave may enhance skin flap survival in an animal model; British Journal of Plastic Surgery; vol. 58, Issue 1, Jan. 2005, pp. 53-57; Copyright 2004; The British Association of Plastic Surgeons, published by Elsevier Ltd.

(Continued)

*Primary Examiner*—Brian Casler
*Assistant Examiner*—John F Ramirez
(74) *Attorney, Agent, or Firm*—David L. King

(57) ABSTRACT

The method of treatment for a periodontal tissue exhibiting a periodontal disease or periodontal condition in a diagnosed patient is disclosed. The method has the steps of activating an acoustic shock wave generator or source to emit acoustic shock waves; and subjecting the periodontal tissue, or the entire periodontal region of the patient to the acoustic shock waves stimulating said tissue, wherein the tissue is positioned within a path of the emitted shock waves. The method of treatment may further have the steps of administering one or more medicaments prior, during or after subjecting the patient to acoustic shock waves or testing the bacterial count or viability of the treated tissue or region of the diagnosed patient after exposure to one or more acoustic shock wave treatments; or subjecting a tissue or organ to a surgical procedure to remove or repair some or all of any defects or degenerative tissues. The method of treatment is for prevention of periodontal disease and may be used with debridement. The treatment is particularly useful in eradicating and inhibiting periodontal biofilms.

23 Claims, 10 Drawing Sheets

U.S. PATENT DOCUMENTS

| | | | |
|---|---|---|---|
| 4,539,989 | A | 9/1985 | Forssmann et al. |
| 4,807,627 | A | 2/1989 | Eisenmenger |
| 4,905,671 | A | 3/1990 | Senge et al. |
| 5,119,801 | A | 6/1992 | Eizenhoefer et al. |
| 5,174,280 | A | 12/1992 | Gruenwald et al. |
| 5,222,484 | A | 6/1993 | Krauss et al. |
| 5,314,457 | A | 5/1994 | Jeutter et al. |
| 5,419,335 | A | 5/1995 | Hartmann |
| 5,545,124 | A | 8/1996 | Krause et al. |
| 5,595,178 | A | 1/1997 | Voss et al. |
| 5,788,496 | A | 8/1998 | Marlinghaus |
| 6,036,661 | A | 3/2000 | Schwarze et al. |
| 6,068,596 | A | 5/2000 | Weth et al. |
| 6,186,963 | B1 | 2/2001 | Schwarze et al. |
| 6,217,531 | B1 | 4/2001 | Reitmajer |
| 6,368,292 | B1 | 4/2002 | Ogden et al. |
| 6,390,995 | B1 | 5/2002 | Ogden et al. |
| 6,726,898 | B2 | 4/2004 | Jernberg |
| 6,777,223 | B2 | 8/2004 | Xu |
| 6,875,422 | B2 | 4/2005 | Nonomura et al. |
| 6,890,900 | B2 | 5/2005 | Braun et al. |
| 2002/0002345 | A1 | 1/2002 | Marlinghaus |
| 2003/0129154 | A1 | 7/2003 | McDaniel |
| 2004/0059265 | A1 | 3/2004 | Candy et al. |
| 2004/0162508 | A1 | 8/2004 | Uebelacker |
| 2005/0010140 | A1 | 1/2005 | Forssmann |
| 2005/0038362 | A1 | 2/2005 | Schultheiss |
| 2005/0075587 | A1 | 4/2005 | Vago |
| 2006/0051328 | A1 | 3/2006 | Johnson |
| 2006/0134016 | A1 * | 6/2006 | Tachibana et al. ............. 424/50 |

FOREIGN PATENT DOCUMENTS

| | | |
|---|---|---|
| DE | 103 11 659 | 9/2004 |
| EP | 0 243 947 A1 | 4/1987 |
| EP | 0 324 711 A2 | 1/1989 |
| EP | 1 445 758 | 8/2004 |
| WO | WO 2005/018600 A2 | 3/2005 |
| WO | WO 2005/063334 A1 | 7/2005 |
| WO | WO 2005/075020 | 8/2005 |

OTHER PUBLICATIONS

T. Nishida, et al; Extracorporeal Cardiac Shock Wave Therapy Markedly Ameliorates Ischemia-Induced Myocardial Dysfunction in Pigs in Vivo; Circulation; Nov. 9, 2004; Circulation. 2004; 110; pp. 3055-3061.

L.Gerdesmeyer, et al; Antibacterial Effects of Extracorporeal Shock Waves;World Fed for Ultrasound in Medicine & Biology; printed USA;Elsevier, vol. 31, No. 1, pp. 115-119, 2005.

G.Haupt, et al; Effect of Shock Waves on the Healing of Partial-Thickness Wounds in Piglets; Journal of Surgical Research, vol. 49, No. 1, pp. 45-48, Jul. 1990 Copyright 1990 by Academic Press, Inc.

Jagadeesh, G. et al;"Novel applications of micro-shock waves in biologival sciences", J. Indian Inst. Sci. 2002, 82, pp. 1-10.

Thiel, M. et al; "The use of shock waves in medicine-a tool of the modern OR; an overview of basic physical principles, history and research", Min Invas Ther & Allied Technol 2000; 9(3/4) 247-253.

Loesche, W and Grossman, N; "Periodontal Disease as a Specific, albeit Chronic, Infection; Diagnosis and Treatment"; Clinical Microbiology Reviews, Oct. 2001, p. 727-752 Copyright 2001; American Society for Microbiology; vol. 14, No. 4.

Huemer, Georg M. et al; " Comparison of the effectiveness of gene therapy with transforming growth factor-B or extracorporal shock wave therapy to reduce ischemic necrosis in an epigastric skin flap model in rats"; From the Clinical Department of Plastic and Reconstructive Surgery, Cardiac Surgery, Orthopedics, and the Ludwig-Boltzmann Institute for Quality Control in Plastic Surgery, Medical University Innsbruck Austria; Feb. 13, 2004; copyright 2005 by the Wound Healing Society. ISSN: 1067-1927 (Wound Rep Reg 2005;13:262-268).

* cited by examiner

METHOD OF TREATMENT FOR AND PREVENTION OF PERIODONTAL DISEASE

RELATED APPLICATIONS

This application is a continuation in part of U.S. patent application Ser. No. 11/122154 filed on May 4, 2005 now U.S. Pat. No. 7,470,240 entitled "Pressure Pulse/Shock Wave Therapy Methods and an Apparatus for Conducting the Therapeutic Methods" and U.S. patent application Ser. No. 11/071156 filed on Mar. 4, 2005 entitled "Pressure Pulse/Shock Wave Apparatus for Generating Waves Having Nearly Plane or Divergent Characteristics" and also claims benefit of priority to U.S. Provisional Patent Application Ser. No. 60/693,143 filed Jun. 23, 2005; U.S. Provisional Patent Application Ser. No. 60/693,369 filed Jun. 22, 2005; U.S. Provisional Patent Application Ser. No. 60/621,028 filed Oct. 22, 2004 and of U.S. Provisional Patent Application Ser. No. 60/642,149 filed Jan. 10, 2005, the disclosures of which are incorporated herein by reference in their entirety.

FIELD OF THE INVENTION

This invention relates to treatments relating to periodontal diseases generally. More specifically to a germicidal and regenerative tooth and bone tissue treatment which can be accomplished post-occurrence or can be used as a dental hygienic preventative treatment.

BACKGROUND OF THE INVENTION

Periodontal diseases are rapidly becoming a major medical concern as populations are living longer.

In an article by Walter J. Loesche and Natalie S. Grossman of the School of Dentistry at the University of Michigan entitled "Periodontal Disease as a Specific, albeit Chronic, Infection: Diagnosis and Treatment" they reported: The prevalence of periodontal disease increases with age and as more people are living longer and retaining more teeth, the number of people developing periodontal disease will increase in the next decades. About 50% of the adult population has gingivitis (gingival inflammation without any bone loss about teeth and no pockets deeper than 3 mm) around three or four teeth at any given time, and 30% have periodontitis as defined by the presence of three or more teeth with pockets of $\geq 4$ mm. Between 5 and 15% of those with periodontitis have advanced forms with pockets of $\geq 6$ mm. Another 3 to 4% of individuals will develop an aggressive form of periodontal disease, known as early onset periodontitis (EOP), between the ages of 14 and 35 years. Any medical condition that affects host antibacterial defense mechanisms, such as human immunodeficiency virus infection HIV, diabetes, and neutrophil disorders, will predispose the individual to periodontal disease.

In that study these University of Michigan scientists concluded that most if not all forms of periodontal diseases are specific, albeit chronic, infections. They note the suppression of these diseases by mechanical debridement and the judicious use of antimicrobial agents targeted against specific anaerobes may be the best antimicrobial treatment known to date and that a huge benefit will be the discovery of really effective treatments which may be stimulated by the fact that periodontal diseases have been linked to cardiovascular disease and stroke.

Their study confirmed that within microbial soup found in infected pockets of the gum are often 500 distinct types of aerobic, anaerobic and microaerobic type organisms with clusters of anaerobic types being the most prevalent suspects in these degenerative diseases. Naturally with such a broad and diverse spectrum of infectious bacteria to treat most antimicrobial treatments have been far from effective.

In U.S. Pat. No. 6,726,898 entitled "Local Delivery of Agents for Disruption and Inhibition of Bacterial Biofilm For Treatment of Periodontal Disease" adds to the discussion by focusing on the fact that plaque is a principal causative agent of periodontal diseases and goes on to suggest plaque and its related buildup is a biofilm that can best be regulated by the use of time release biodegradable microspheres for sustained, controlled delivery or agents to disrupt and inhibit the formation of biofilms at localized periodontal treatment sites.

He suggests insertion of biodegradable microspheres containing agents active against bacterial biofilms into the gingival crevices or pocket regions.

The apparent frustration that results in the use of microbial antibiotics to fight periodontal diseases caused by bacteria laden biofilms is the bacteria's ability to adapt even mutate to wherein these medicinal drugs have little or no effect. Accordingly the use of such antibiotic treatments is used only in last resort cases wherein the host patient has virtually no other viable recourse.

This puts the dental and medical community at a disadvantage in that effective and long term solutions do not appear available. Treatments that may only strengthen and stimulate anaerobic mutations that may be worse to control significantly limits the treatment options.

An objective of the present invention is to provide a treatment option that can germicidally eradicate bacterial formation including biofilms either as a stand alone treatment or in conjunction with debridement procedures or medications.

Another objective of the present invention is to provide a method of periodontal treatments that can repair damaged tissue and regenerate new growth of tissue in a degenerative condition.

This and other objectives are described in the description as follows.

SUMMARY OF THE INVENTION

The method of treatment for a periodontal tissue exhibiting a periodontal disease or periodontal condition in a diagnosed patient is disclosed. The method has the steps of activating an acoustic shock wave generator or source to emit acoustic shock waves; and subjecting the periodontal tissue, or the entire periodontal region of the patient to the acoustic shock waves stimulating said tissue, wherein the tissue is positioned within a path of the emitted shock waves. The emitted shock waves are either convergent, divergent, planar or near planar. Alternatively the emitted shock waves can be convergent having one or more geometric focal volumes or points at a distance of at least X from the generator or source, the method further comprising positioning the organ at a distance at or less than the distance X from the source.

The method of treatment may further have the steps of administering one or more medicaments prior, during or after subjecting the patient to acoustic shock waves or testing the bacterial count or viability of the treated tissue or region of the diagnosed patient after exposure to one or more acoustic shock wave treatments; or subjecting a tissue to a surgical procedure to remove or repair some or all of any defects or degenerative tissues. The treated periodontal tissue may have an indication of one or more pathological conditions including: a periodontal biofilm mass, periapical endodontic lesions, endo-perio lesions, gingivitis, inflammation of gingival tissue, periodontitis, progressive loss of ligament, cementum or alveolar bone support to teeth. Also, the treated tissue may have one or more conditions requiring treatment as follows: ridge augmentation for cosmetic, prosthetic or implantation of teeth; to assist osteoblastic and osteoclastic processes in orthodontia; regeneration of alveolar bone surrounding loose teeth implants regeneration of structures supporting the teeth including regeneration of structures supporting teeth including gingival, periodontal ligament, cementum and alveolar bone. The method of treatment is for prevention of periodontal disease and may be used with debridement.

In most if not all cases the treatment includes the step of destroying biofilm in or on the treated tissue or region, wherein the treated tissue or region activates or otherwise stimulates stem cells or release of cellular growth factors in the oral structure effecting a tissue repair or tissue regeneration.

DEFINITIONS

"aerobic" living, active, or occurring only in the presence of oxygen.

"alveolar" Alveolar bone the part of the jaw that surround the roots of the teeth. Alveolar process the curving part of the jaw into which the teeth are rooted. Alveolus the socket in the alveolar bone into which the tooth's root fits.

"anaerobic" living, active, or occurring in the absence of free oxygen.

"apoptosis" is the biological process of controlled, programmed cell death, by means of which cells die by a process of condensation without the release of cell contents into the surrounding milieu.

"cementum" the very thin, bonelike structure that covers the root of the tooth.

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"cystic fibrosis" a common disease especially in Caucasian populations that appears usually in early childhood, is inherited as a recessive monogenic trait, involves functional disorder of the exocrine glands, and is marked especially by faulty digestion due to a deficiency of pancreatic enzymes, by difficulty in breathing due to mucus accumulation in airways, and by excessive loss of salt in the sweat.

"cytoplasm" The part of a cell that contains the CYTOSOL and small structures excluding the CELL NUCLEUS; MITOCHONDRIA; and large VACUOLES.

"debridement" the surgical removal of lacerated, devitalized, or contaminated tissue. This includes removal of tartar beneath the gum and scaling and root planing and in more advanced conditions may necessitate periodontal surgery or complete debridement of the roots and re-contouring of the hard and soft tissue to arrest the disease process or to restore lost bone.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different ways, for example: A focused wave will become divergent once it has passed through the focal point. Spherical waves are also included in this definition of divergent waves and have wave fronts with divergent characteristics.

"endocarditis" inflammation of the lining of the heart and its valves.

"endo-perio lesions" lesions due to inflammatory products found in varying degrees in both the periodontium and the pulpal tissues.

"extracorporeal" occurring or based outside the living body.

A "generalized paraboloid" according to the present invention is also a three-dimensional bowl. In two dimensions (in Cartesian coordinates, x and y) the formula $y^n=2px$ [with n being ≠2, but being greater than about 1.2 and smaller than 2, or greater than 2 but smaller than about 2.8]. In a generalized paraboloid, the characteristics of the wave fronts created by electrodes located within the generalized paraboloid may be corrected by the selection of (p (−z,+z)), with z being a measure for the burn down of an electrode, and n, so that phenomena including, but not limited to, burn down of the tip of an electrode (−z,+z) and/or disturbances caused by diffraction at the aperture of the paraboloid are compensated for.

"gingivitis" inflammation of gingival tissue without loss of connective tissue. The earliest sign is bleeding gum. Gingiva soft tissues overlying the crowns of unerupted teeth and encircling the necks of those that have erupted. Gingival Hyperplasia an overgrowth of gingival tissues.

"lactate dehydrogenase (LDH)" A tetrameric enzyme that, along with the coenzyme NAD+, catalyzes the interconversion of lactate and pyruvate. In vertebrates, genes for three different subunits (LDH-A, LDH-B and LDH-C) exist.

"mitochondria" Semiautonomous, self-reproducing organelles that occur in the cytoplasm of all cells of most, but not all, eukaryotes. Each mitochondrion is surrounded by a double limiting membrane. The inner membrane is highly invaginated, and its projections are called cristae. Mitochondria are the sites of the reactions of oxidative phosphorylation, which result in the formation of ATP. They contain distinctive RIBOSOMES, transfer RNAs (RNA, TRANSFER); AMINO ACYL T RNA SYNTHETASES; and elongation and termination factors. Mitochondria depend upon genes within the nucleus of the cells in which they reside for many essential messenger RNAs (RNA, MESSENGER). Mitochondria are believed to have arisen from aerobic bacteria that established a symbiotic relationship with primitive protoeukaryotes.

"necrosis" A pathological process caused by the progressive degradative action of enzymes that is generally associated with severe cellular trauma. It is characterized by mitochondrial swelling, nuclear flocculation, uncontrolled cell lysis, and ultimately CELL DEATH.

A "paraboloid" according to the present invention is a three-dimensional reflecting bowl. In two dimensions (in Cartesian coordinates, x and y) the formula $y^2=2px$, wherein p/2 is the distance of the focal point of the paraboloid from its apex, defines the paraboloid. Rotation of the two-dimensional figure defined by this formula around its longitudinal axis generates a de facto paraboloid.

"periapical endodontic lesions" lesions in the area at the end of the roots of the teeth.

"periodontitis" inflammation of the supporting structures of the tooth, including the gum, the periodontal ligament, and the jawbone.

"phagocytosis" The engulfing of microorganisms, other cells, and foreign particles by phagocytic cells.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milli-seconds (ins). Very fast pressure pulses are called shock waves. Shock waves used in medical applications do have amplitudes above 0.1 MPa and rise times of the amplitude are below 100's of ns. The duration of a shock wave is typically below 1-3 micro-seconds ($\mu s$) for the positive part of a cycle and typically above some micro-seconds for the negative part of a cycle.

Waves/wave fronts described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

BRIEF DESCRIPTION OF THE DRAWINGS

The invention will be described by way of example and with reference to the accompanying drawings in which.

DETAILED DESCRIPTION OF THE INVENTION

The present invention relates to the use of various therapeutic pressure pulse wave patterns or acoustic shock wave patterns as illustrated in FIGS. 1-12 for treating various periodontal diseases or conditions or for preventing such conditions from occurring. Each illustrated wave pattern will be discussed later in the description, however, the use of each has particularly interesting beneficial features that are a remarkably valuable new tool in the fight against periodontal diseases.

Figure 13:
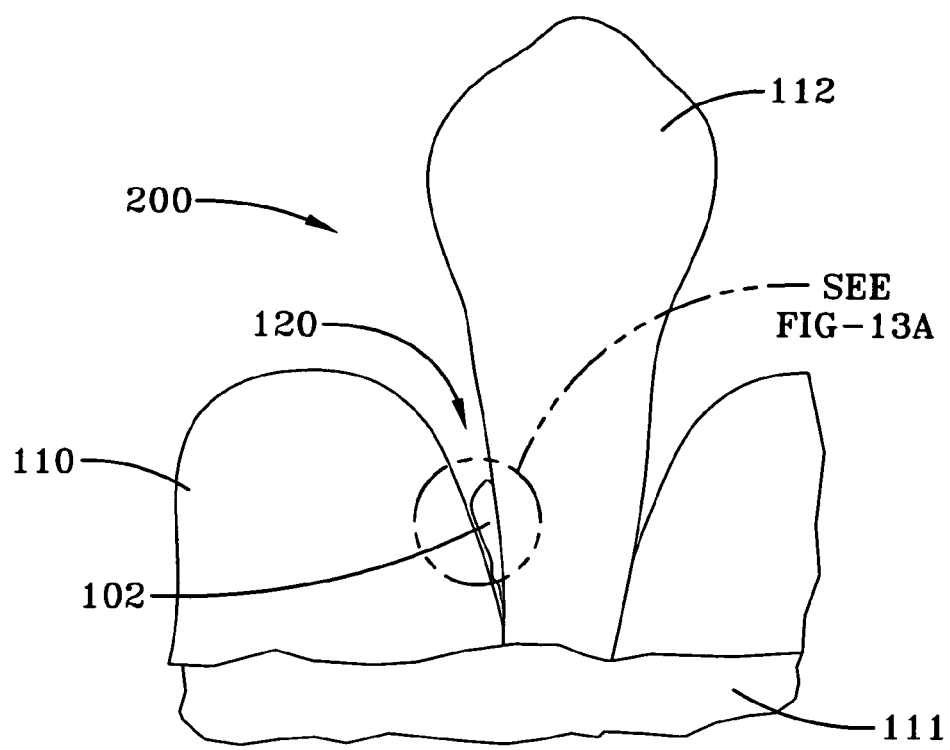
FIG. 13 is a perspective view of a portion of the periodontal region showing the tooth, gum and biofilm buildup of plaque.
Figure 13A:
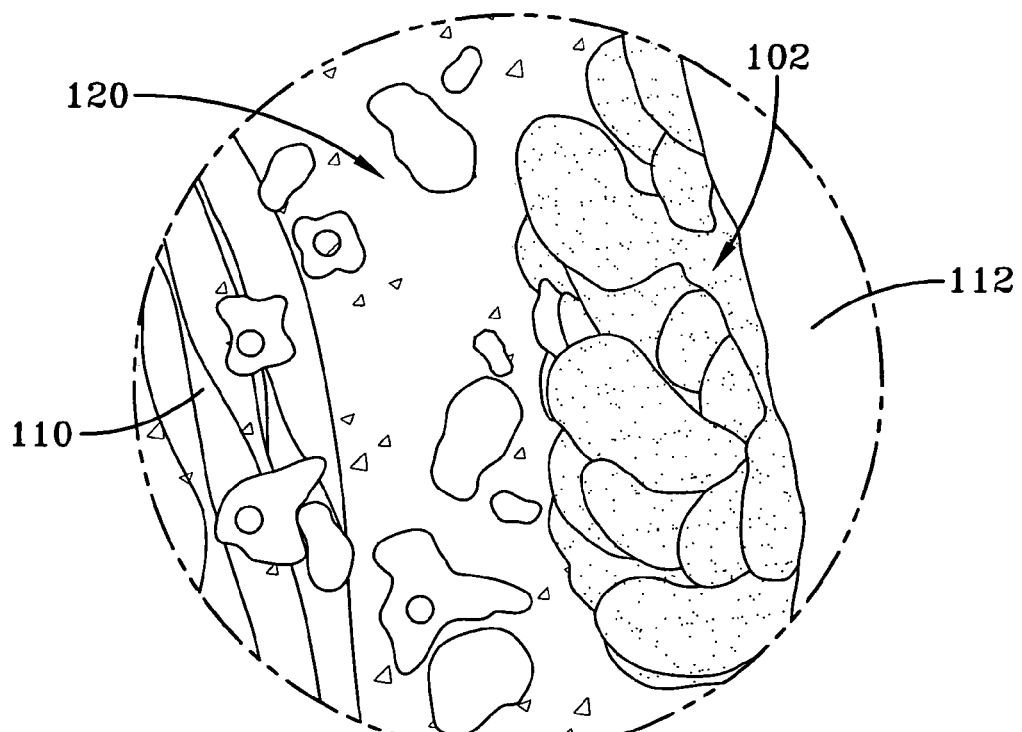
FIG. 13a is an enlarged view of the gingival crevice.

With reference to FIGS. 13 and 13A, a perspective view of a portion of the periodontal region 200 is shown. The gingival tissue 100, more commonly referred to as the gums 110, and the underlying alveolar (socket) bone 111 supports the teeth 112. In a region between the teeth 112 and the gums 110 called the gingival crevice area 120 is a region in which bacteria colonize on tooth surfaces to form bacterial plaque biofilms 102 which is the principal source of periodontal diseases.

The current preventive procedure used to eliminate bacterial plaque is periodic tooth cleaning procedures which involve mechanically shearing the accretions of plaque from the tooth structure. This mechanical treatment is called debridement and at best its use is of a transient benefit as the bacteria simply re-colonize the root surface. Accordingly periodic teeth cleaning is best performed at least twice a year.

In dentistry, a current treatment can be ultrasonic debridement which is practiced using a relatively blunt metal tipped instrument that is applied to the root surface below the gum line. The metal tip vibrates at ultrasonic frequencies and breaks the calculus (tartar) attachment to the root of the tooth. Calculus is the hardened substance that attaches to both the tooth structure above and below the gum line. The ultrasonic tip is used in both areas. Patients with periodontal disease typically have sub and supra-gingival calculus, but not always. Once the calculus is removed, it is hoped that the tissue (bone, ligament, gingival) will regenerate, but this is very often not the case. The next step in current treatment is surgery.

Shock waves are a completely different technology and a quantum leap beyond ultrasonic debridement. The mechanism of shock waves is far from being understood, but is known to cause new blood vessels to grow in an area of treatment and regenerate bony tissue. In the present invention shock waves are used to treat periodontal disease by causing the structure of the bone, ligament attachment of root to bone and tissue architecture to be regenerated. This is a phenomenal advancement in the current approach which includes difficult surgery. If surgery could be replaced in many cases, it would save millions of dollars, gain wide acceptance (non-invasive) and be a tremendous boon to patients world wide. The anaerobic sub-gingival bacteria (oxygen-hating below the gum) are thought to be the major culprit in periodontal disease. These anaerobes are commonly found in periodontal biofilms.

Ideally the treatments to remove the bacterial plaque would not only eradicate the bacteria, but would also provide or stimulate a germicidal protective feature that would inhibit the bacteria from re-colonizing these regions.

The time release of microspheres of medicaments placed in the gingival crevice area as described in U.S. Pat. No. 6,726,898 was an attempt at this inhibiting effect.

As was mentioned the use of antibiotics has its own detrimental drawbacks and is thus far more complicated and less effective than needed in the area of treating these complex periodontal biofilms.

The present invention employs the use of pressure pulses or shock waves to stimulate a germicidal cellular response that kills the bacteria laden periodontal biofilms while stimulating a tissue regenerative healing process that activates the tissue cells to defend against these microbial agents.

Figure 14:
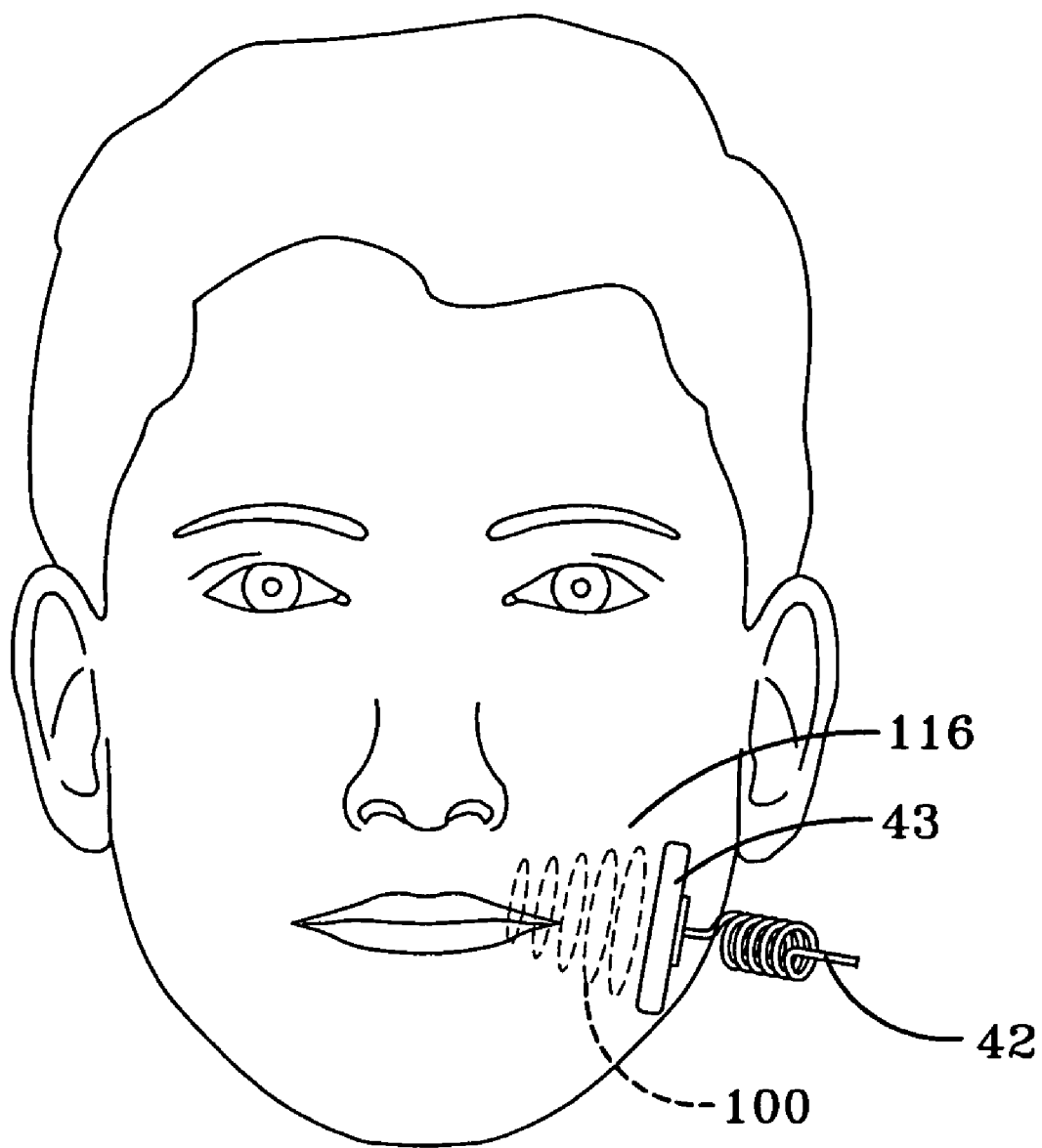
FIG. 14 shows a patient being treated extracorporeally with shock waves being transmitted through the skin tissue to the periodontal region to be treated.

In the pressure pulse or shock wave method of treating a tissue, an organ or the entire body of a host be it mechanical system or a mammal, the host system or mammal be it human or an animal with a risk of exposure to a periodontal biofilm or post-occurrence of such periodontal biofilms requires the host patient to be positioned in a convenient orientation to permit the source of the emitted waves to most directly send the waves to the target site to initiate pressure pulse or shock wave stimulation of the target area with minimal, preferably no obstructing features in the path of the emitting source or lens. Assuming the treatment region is accessible through the mouth then the shock wave head 43 can be inserted and placed directly on the treatment region. Alternatively the shock wave head 43 can be placed externally on the skin and transmit the emitted shock wave patterns through the cheek tissue 116 for example and into the adjacent gingival tissue 100 to be treated, as shown in FIG. 14. Preferably the outer skin tissue is pressed against the treatment region to insure the transmission loss is minimal. In some cases the gums or teeth may benefit or require numbing prior to treatment. This is particularly true if the use of high energy focused waves are being transmitted that stimulate the sensitive nerves in the treatment area. Assuming the periodontal biofilm target area or site is within a projected area of the wave transmission, a single transmission dosage of wave energy may be used. The transmission dosage can be from a few seconds to 20 minutes or more dependent on the condition. Preferably the waves are generated from an unfocused or focused source. The unfocused waves can be divergent, planar or near planar and having a low pressure amplitude and density in the range of 0.00001 mJ/mm$^2$ to 1.0 mJ/mm$^2$ or less, most typically below 0.2 mJ/mm$^2$. The focused source preferably can use a diffusing lens or have a far-sight focus to minimize if not eliminate having the localized focus point within the tissue. Preferably the focused shock waves are used at a similarly effective low energy transmission or alternatively can be at higher energy but wherein the tissue target site is disposed pre-convergence inward of the geometric focal point of the emitted wave transmission. In treating some hard to penetrate periodontal biofilms, the pressure pulse more preferably is a high energy target focused wave pattern which can effectively attack the biofilm outer structure or barrier shield causing fractures or openings to be created to expose the colonies of microorganisms within the biofilm to the germicidal effects of the pressure pulses or shock waves. This emitted energy destroys the underlying microorganism's cellular membranes. In addition the fragmentation of the biofilms outer barrier is then easily absorbed by or flushed out of the host. The surrounding healthy cells in the region treated are activated initiating a defense mechanism response to assist in eradication of the unwanted infection.

These shock wave energy transmissions are effective in stimulating a cellular response and can be accomplished without creating the cavitation bubbles in the tissue of the target site when employed in other than high energy focused transmissions. This effectively insures the tissue or organ does not have to experience the sensation of hemorrhaging so common in the higher energy focused wave forms having a focal point at or within the targeted treatment site.

If the target site is an organ subjected to a surgical procedure exposing at least some if not all of the organ within the body cavity the target site may be such that the patient or the generating source must be reoriented relative to the site and a second, third or more treatment dosage can be administered. The fact that some if not all of the dosage can be at a low energy the common problem of localized hemorrhaging is reduced making it more practical to administer multiple dosages of waves from various orientations to further optimize the treatment and cellular stimulation of the target site. Heretofore focused high energy multiple treatments induced pain and discomfort to the patient. The use of low energy focused or un-focused waves at the target site enables multiple sequential treatments.

The present method may need precise site location and can be used in combination with such known devices as ultrasound, cat-scan or x-ray imaging if needed. The physician's general understanding of the anatomy of the patient may be sufficient to locate the target area to be treated. This is particularly true when the exposed tissue or portion of the infected body or organ is visually within the surgeon's line of sight and this permits the lens or cover of the emitting shock wave source to impinge on the affected organ or tissue directly or through a transmission enhancing gel, water or fluid medium during the pressure pulse or shock wave treatment. The treated area can withstand a far greater number of shock waves based on the selected energy level being emitted. For example at very low energy levels the stimulation exposure can be provided over prolonged periods as much as 20 minutes if so desired. At higher energy levels the treatment duration can be shortened to less than a minute, less than a second if so desired. The limiting factor in the selected treatment dosage is avoidance or minimization of surrounding cell hemorrhaging and other kinds of damage to the surrounding cells or tissue while still providing a stimulating stem cell activation or a cellular release or activation of VEGF and other growth factors while simultaneously germicidally attacking the periodontal biofilm barrier and underlying colony of microorganisms.

Due to the wide range of beneficial treatments available it is believed preferable that the optimal use of one or more wave generators or sources should be selected on the basis of the specific application. Wherein relatively small target sites may involve a single wave generator placed on an adjustable manipulator arm. A key advantage of the present inventive methodology is that it is complimentary to conventional medical procedures. In the case of any operative surgical procedure the surgical area of the patient can be bombarded with these energy waves to stimulate cellular release of healing agents and growth factors. This will dramatically reduce the healing process time. Most preferably such patients may be provided more than one such treatment with an intervening dwell time for cellular relaxation prior to secondary and tertiary post operative treatments.

The underlying principle of these pressure pulse or shock wave therapy methods is to attack the periodontal biofilm directly and to stimulate the body's own natural healing capability. This is accomplished by deploying shock waves to stimulate strong cells in the surrounding tissue to activate a variety of responses. The acoustic shock waves transmit or trigger what appears to be a cellular communication throughout the entire anatomical structure, this activates a generalized cellular response at the treatment site, in particular, but more interestingly a systemic response in areas more removed from the wave form pattern. This is believed to be one of the reasons molecular stimulation can be conducted at threshold energies heretofore believed to be well below those commonly accepted as required. Accordingly not only can the energy intensity be reduced in some cases, but also the number of applied shock wave impulses can be lowered from several thousand to as few as one or more pulses and still yield a beneficial stimulating response. The key is to provide at least a sufficient amount of energy to weaken the periodontal biofilms protective outer barrier or shield. This weakening can be achieved by any fracture or opening that exposes the underlying colony of microorganisms.

The use of shock waves as described above appears to involve factors such as thermal heating, light emission, electromagnetic field exposure, chemical releases in the cells as well as a microbiological response within the cells. Which combination of these factors plays a role in stimulating healing is not yet resolved. However, there appears to be a commonality in the fact that growth factors are released which applicants find indicative that otherwise dormant cells within the tissue appear to be activated which leads to the remarkable ability of the targeted periodontal tissue to generate new growth or to regenerate weakened vascular networks or blood circulation in for example the gingival tissue. This finding leads to a complimentary use of shock wave therapy in combination with stem cell therapies that effectively activate or trigger stem cells to more rapidly replicate enhancing the ability to harvest and culture more viable cells from the placenta, a nutrient culture of said stem cells, or other sources. The ability to stimulate stein cells can occur within the patients own body activating the naturally occurring stein cells or stem cells that have been introduced to the patient as part of a treatment beneficially utilizing stem cells. This is a significant clinical value in its own right.

In one embodiment, the invention provides for germicidal cleaning of periodontal biofilm diseased or infected areas and for wound cleaning generally after exposure to surgical procedures.

The use of shock wave therapy requires a fundamental understanding of focused and unfocused shock waves, coupled with a more accurate biological or molecular model.

Focused shock waves are focused using ellipsoidal reflectors in electromechanical sources from a cylindrical surface or by the use of concave or convex lenses. Piezoelectric sources often use spherical surfaces to emit acoustic pressure waves which are self focused and have also been used in spherical electromagnetic devices.

The biological model proposed by co-inventor Wolfgang Schaden provides a whole array of clinically significant uses of shock wave therapy.

Accepting the biological model as promoted by W. Schaden, the peak pressure and the energy density of the shock waves can be lowered dramatically. Activation of the body's healing mechanisms will be seen by in growth of new blood vessels and the release of growth factors.

The biological model motivated the design of sources with low pressure amplitudes and energy densities. First: spherical waves generated between two tips of an electrode; and second: nearly even waves generated by generalized parabolic reflectors. Third: divergent shock front characteristics are generated by an ellipsoid behind f2. Unfocused sources are preferably designed for extended two dimensional areas/volumes like skin. The unfocused sources can provide a divergent wave pattern a planar or a nearly planar wave pattern and can be used in isolation or in combination with focused wave patterns yielding to an improved therapeutic treatment capability that is non-invasive with few if any disadvantageous contraindications. Alternatively a focused wave emitting treatment may be used wherein the focal point extends preferably beyond the target treatment site, potentially external to the patient. This results in the reduction of or elimination of a localized intensity zone with associated noticeable pain effect while providing a wide or enlarged treatment volume at a variety of depths more closely associated with high energy focused wave treatment. The utilization of a diffuser type lens or a shifted far-sighted focal point for the ellipsoidal reflector enables the spreading of the wave energy to effectively create a convergent but off target focal point. This insures less tissue trauma while insuring cellular stimulation to enhance the healing process and control the migration or spreading of the infection within the host. More preferably if a resident periodontal biofilm location can be isolated and a short, but high energy focused wave pattern can be emitted on the outer barrier of the biofilm causing a fracture or fragmentation in the outer barrier and then a lower unfocused energy transmission can be applied to provide an overall germicidal treatment and surrounding cell stimulation to destroy the biofilm infected periodontal site and eradicate the resultant microbial debris.

This method of treatment has the steps of, locating a periodontal biofilm treatment site, region or location, generating either focused, convergent diffused or far-sighted focused shock waves or unfocused shock waves; directing these shock waves to the periodontal biofilm treatment site; and applying a sufficient number of these shock waves to induce an outer barrier biofilm weakening while simultaneously activating one or more growth factors in the surrounding tissue cells thereby inducing or accelerating healing.

The unfocused shock waves can be of a divergent wave pattern, planar or near planar pattern preferably convergent diffused or far-sighted wave pattern, of a low peak pressure amplitude and density. Typically the energy density values range as low as 0.000001 mJ/mm$^2$ and having a high end energy density of below 1.0 mJ/mm$^2$, preferably 0.20 mJ/mm$^2$ or less. The peak pressure amplitude of the positive part of the cycle should be above 1.0 and its duration is below 1-3 microseconds.

The treatment depth can vary from the surface to the full depth of the treated organ. The treatment site can be defined by a much larger treatment area than the 0.10-3.0 cm$^2$ commonly produced by focused waves. The above methodology is particularly well suited for surface as well as sub-surface soft tissue organ treatments.

The above methodology is valuable in generation of tissue, vascularization and may be used in combination with stem cell therapies as well as regeneration of tissue and vascularization.

The methodology is useful in (re)vascularization and regeneration of not only periodontal tissue such as the teeth and gums, but also the heart, brain, liver, kidney, skin, urological organs, reproductive organs and digestive tract.

The methodology is useful in stimulating enforcement of defense mechanisms in tissue cells to fight infections from bacteria and can be used germicidally to treat or cleanse wounds or other biofilm target sites which is a primary concern in the case of treating human diseases such as native valve endocarditis, cystic fibrosis, periodontal gum disease and urinary or digestive tract infections resulting from such exposures to biofilm type agents.

While the above listed indications cited above are not exhaustive nor intended to be limiting, it is exemplary of the wide range of beneficial uses of high energy focused or low energy and amplitude unfocused divergent, planar or nearly planar shock waves, convergent shock waves, diffused shock waves or a combination of shock wave types in the treatment of humans and other mammals that are exposed to a biofilm type infection or are at high risk to be so exposed as the result of a high potential risk to such biofilm infectious exposure.

A most significant method of preventive medicine can be practiced that is fully enabled by the use of these relatively low amplitude and pressure shock waves. The method includes the steps of identifying high risk patients for a variety of potential risk conditions. Such condition could be by way of example leaking heart valves, urinary infections, degenerative gum disease or cystic fibrosis. After identifying a risk prone candidate providing one or a series of two or more exposure treatments with focused or unfocused, divergent, planar or near planar shock waves or convergent far-sighted focused shock waves or diffused shock waves to the treatment site, in this example the region surrounding or in proximity to a biofilm occurrence risk location. Then after treatments the physician can optionally ultrasound visually or otherwise determine the increase in regeneration or vascularization in the treated tissue after a period of time. Assuming an initial baseline determination of the tissue regeneration or vascularization had been initially conducted an estimate or calculation of dosage requirements can be made. This procedure can be used for any biofilm at risk condition. After a surgical repair procedure the surrounding tissues can be post-operatively shock wave treated as well.

The implications of using the (re)generative features of this type of shock wave therapy are any biofilm weakened organ or tissue even teeth or bone can be strengthened to the point of reducing or eliminating the risk of irreparable damage or failure as a result of microbial infections.

The stimulation of growth factors and activation of healing acceleration within the cells of the treated tissues is particularly valuable to host patients and other high risk factor subjects wherein conventional antibiotic treatments have been unsuccessful.

Even more striking as mentioned earlier, early prevention therapies can be employed to stimulate tissue or organ modeling to be maintained within acceptable ranges prior to an exposure to biofilm infections. This is extremely valuable in the prevention of spreading the infection for example. The methods would be to identify at risk patients with a known biofilm exposure risk, and subjecting that patient to therapeutic shock wave therapy for the purpose of stimulating tissue repair or regeneration effectively remodeling the patient's susceptible organs to be within accepted functional parameters prior to exposure to a biofilm infection. The objective being to preventively stimulate cellular tissue repairs to preemptively avoid a degenerative condition from occurring which may result in the onset of an antibiotic resistant infection which can require invasive surgical procedures.

This preventive therapy is most needed to combat biofilm exposure which left untreated results in cellular destruction or any other degenerative conditions. In the area of dental cleaning appointments or a dental prophylaxis or prophy, the use of pressure pulse waves or acoustic shock waves can be administered by a trained dental hygienist. Unlike current ultrasonic cleaning now available; the acoustic shock wave provides a far more advanced tissue stimulation which activates a germicidal response that continues for many weeks after treatment and thus is a natural defense method of healing that in most cases of periodontal biofilm exposure would not need supplemental antibiotics.

Figure 1A:
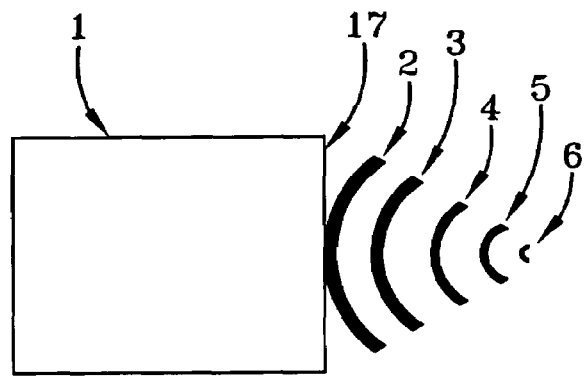
FIG. 1a is a simplified depiction of a pressure pulse/shock wave (PP/SW) generator with focusing wave characteristics.
Figure 1B:
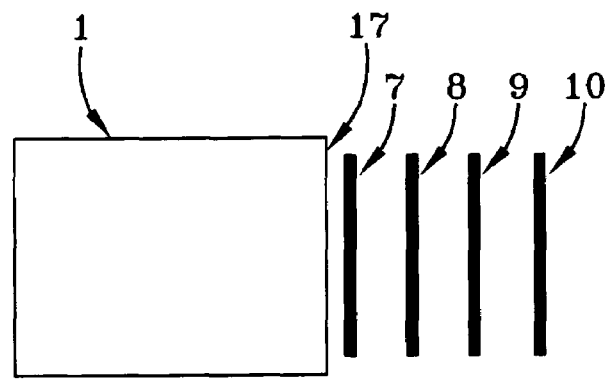
FIG. 1b is a simplified depiction of a pressure pulse/shock wave generator with plane wave characteristics.

FIG. 1$a$ is a simplified depiction of the a pressure pulse/shock wave (PP/SW) generator, such as a shock wave head, showing focusing characteristics of transmitted acoustic pressure pulses. Numeral 1 indicates the position of a generalized pressure pulse generator, which generates the pressure pulse and, via a focusing element, focuses it outside the housing to treat diseases. The affected tissue or organ is generally located in or near the focal point which is located in or near position 6. At position 17 a water cushion or any other kind of exit window for the acoustical energy is located.

FIG. 1$b$ is a simplified depiction of a pressure pulse/shock wave generator, such as a shock wave head, with plane wave characteristics. Numeral 1 indicates the position of a pressure pulse generator according to the present invention, which generates a pressure pulse which is leaving the housing at the position 17, which may be a water cushion or any other kind of exit window. Somewhat even (also referred to herein as "disturbed") wave characteristics can be generated, in case a paraboloid is used as a reflecting element, with a point source (e.g. electrode) that is located in the focal point of the paraboloid. The waves will be transmitted into the patient's body via a coupling media such as, e.g., ultrasound gel or oil and their amplitudes will be attenuated with increasing distance from the exit window 17.

Figure 1C:
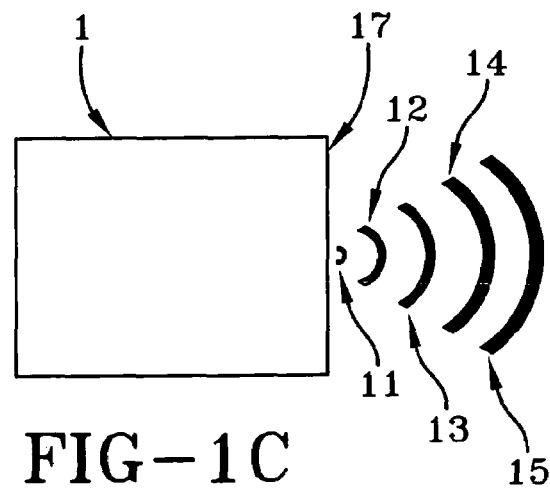
FIG. 1c is a simplified depiction of a pressure pulse/shock wave generator with divergent wave characteristics.

FIG. 1c is a simplified depiction of a pressure pulse shock wave generator (shock wave head) with divergent wave characteristics. The divergent wave fronts may be leaving the exit window 17 at point 11 where the amplitude of the wave front is very high. This point 17 could be regarded as the source point for the pressure pulses. In FIG. 1c the pressure pulse source may be a point source, that is, the pressure pulse may be generated by an electrical discharge of an electrode under water between electrode tips. However, the pressure pulse may also be generated, for example, by an explosion, referred to as a ballistic pressure pulse. The divergent characteristics of the wave front may be a consequence of the mechanical setup shown in FIG. 2b.

Figure 2A:
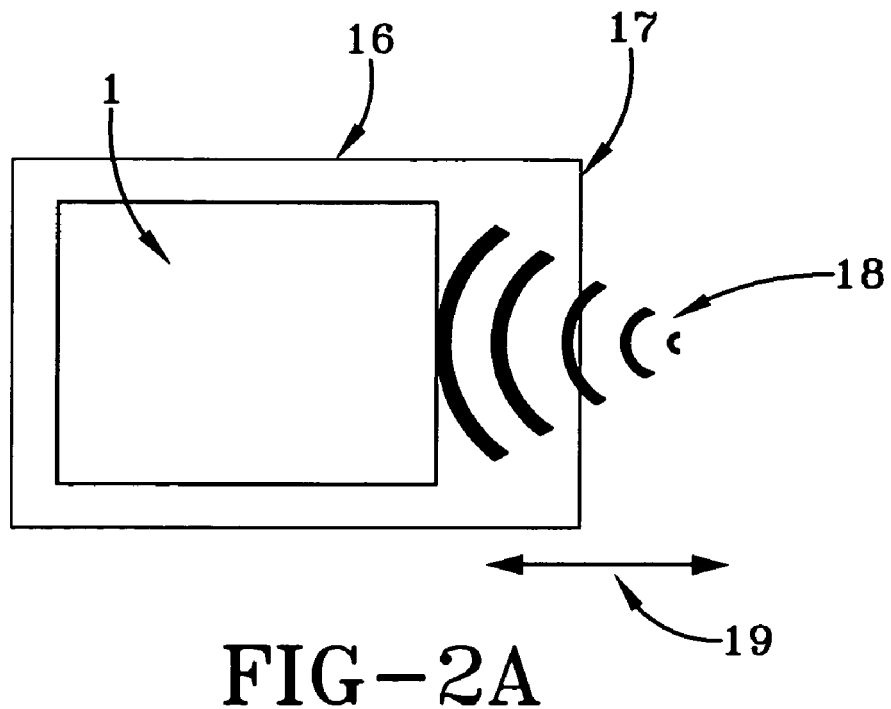
FIG. 2a is a simplified depiction of a pressure pulse/shock wave generator having an adjustable exit window along the pressure wave path. The exit window is shown in a focusing position.

FIG. 2a is a simplified depiction of a pressure pulse/shock wave generator (shock wave head) according to the present invention having an adjustable or exchangeable (collectively referred to herein as "movable") housing around the pressure wave path. The apparatus is shown in a focusing position. FIG. 2a is similar to FIG. 1a but depicts an outer housing (16) in which the acoustical pathway (pressure wave path) is located. In a preferred embodiment, this pathway is defined by especially treated water (for example, temperature controlled, conductivity and gas content adjusted water) and is Within a water cushion or within a housing having a permeable membrane, which is acoustically favorable for the transmission of the acoustical pulses. In certain embodiments, a complete outer housing (16) around the pressure pulse/shock wave generator (1) may be adjusted by moving this housing (16) in relation to, e.g., the focusing element in the generator. However, as the person skilled in the art will appreciate, this is only one of many embodiments of the present invention. While the figure shows that the exit window (17) may be adjusted by a movement of the complete housing (16) relative to the focusing element, it is clear that a similar, if not the same, effect can be achieved by only moving the exit window, or, in the case of a water cushion, by filling more water in the volume between the focusing element and the cushion. FIG. 2a shows the situation in which the arrangement transmits focused pressure pulses.

Figure 2B:
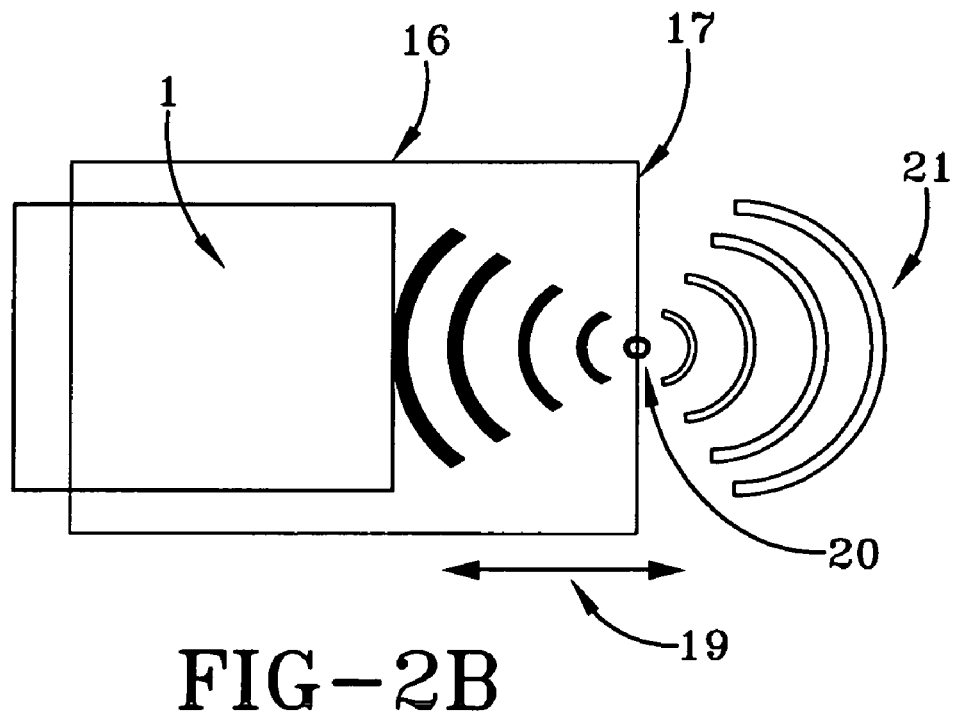
FIG. 2b is a simplified depiction of a pressure pulse/shock wave generator having an exit window along the pressure wave path. The exit window as shown is positioned at the highest energy divergent position.

FIG. 2b is a simplified depiction of the pressure pulse/ shock wave generator (shock wave head) having an adjustable or exchangeable housing around the pressure wave path with the exit window 17 being in the highest energy divergent position. The configuration shown in FIG. 2b can, for example, be generated by moving the housing (16) including the exit window (17), or only the exit window (17) of a water cushion, towards the right (as shown in the Figure) to the second focus f2 (20) of the acoustic waves. In a preferred embodiment, the energy at the exit window will be maximal. Behind the focal point, the waves may be moving with divergent characteristics (21).

Figure 2C:
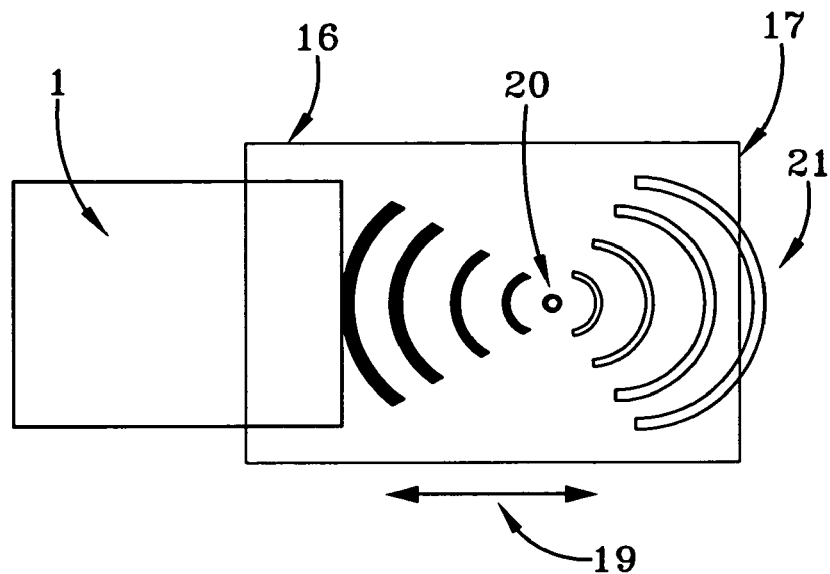
FIG. 2c is a simplified depiction of a pressure pulse/shock wave generator having an exit window along the pressure wave path. The exit window is shown at a low energy divergent position.

FIG. 2c is a simplified depiction of the pressure pulse/ shock wave generator (shock wave head) having an adjustable or exchangeable housing around the pressure wave path in a low energy divergent position. The adjustable housing or water cushion is moved or expanded much beyond f2 position (20) so that highly divergent wave fronts with low energy density values are leaving the exit window (17) and may be coupled to a patient's body. Thus, an appropriate adjustment can change the energy density of a wave front without changing its characteristic.

This apparatus may, in certain embodiments, be adjusted/ modified/or the complete shock wave head or part of it may be exchanged so that the desired and/or optimal acoustic profile such as one having wave fronts with focused, planar, nearly plane, convergent or divergent characteristics can be chosen.

A change of the wave front characteristics may, for example, be achieved by changing the distance of the exit acoustic window relative to the reflector, by changing the reflector geometry, by introducing certain lenses or by removing elements such as lenses that modify the waves produced by a pressure pulse/shock wave generating element. Exemplary pressure pulse/shock wave sources that can, for example, be exchanged for each other to allow an apparatus to generate waves having different wave front characteristics are described in detail below.

In certain embodiments, the change of the distance of the exit acoustic window can be accomplished by a sliding movement. However, in other embodiments of the present invention, in particular, if mechanical complex arrangements, the movement can be an exchange of mechanical elements.

In one embodiment, mechanical elements that are exchanged to achieve a change in wave front characteristics include the primary pressure pulse generating element, the focusing element, the reflecting element, the housing and the membrane. In another embodiment, the mechanical elements further include a closed fluid volume within the housing in which the pressure pulse is formed and transmitted through the exit window.

In one embodiment, the apparatus of the present invention is used in combination therapy. Here, the characteristics of waves emitted by the apparatus are switched from, for example, focused to divergent or from divergent with lower energy density to divergent with higher energy density. Thus, effects of a pressure pulse treatment can be optimized by using waves having different characteristics and/or energy densities, respectively.

While the above described universal toolbox of the present invention provides versatility, the person skilled in the art will appreciate that apparatuses that only produce waves having, for example, nearly plane characteristics, are less mechanically demanding and fulfill the requirements of many users.

As the person skilled in the art will also appreciate that embodiments shown in the drawings are independent of the generation principle and thus are valid for not only electrohydraulic shock wave generation but also for, but not limited to, PP/SW generation based on electromagnetic, piezoceramic and ballistic principles. The pressure pulse generators may, in certain embodiments, be equipped with a water cushion that houses water which defines the path of pressure pulse waves that is, through which those waves are transmitted. In a preferred embodiment, a patient is coupled via ultrasound gel or oil to the acoustic exit window (17), which can, for example, be an acoustic transparent membrane, a water cushion, a plastic plate or a metal plate.

Figure 3:
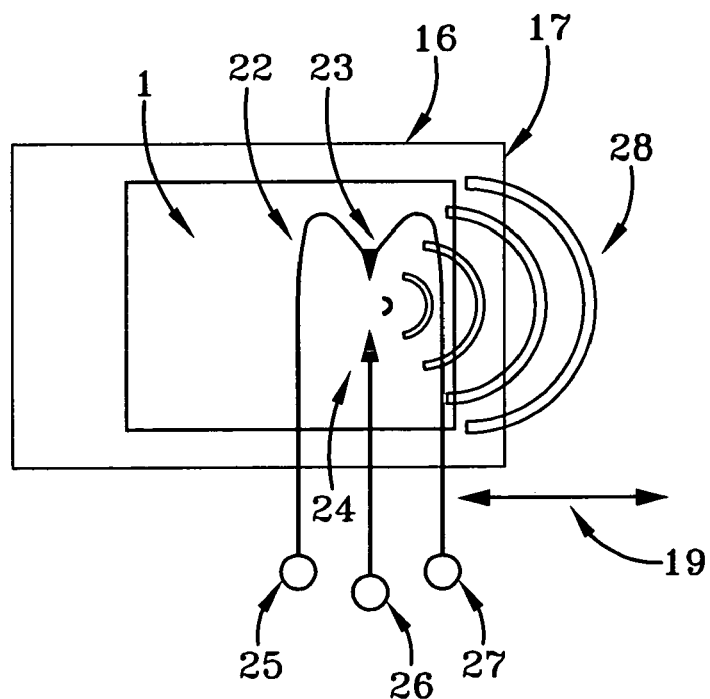
FIG. 3 is a simplified depiction of an electro-hydraulic pressure pulse/shock wave generator having no reflector or focusing element. Thus, the waves of the generator did not pass through a focusing element prior to exiting it.

FIG. 3 is a simplified depiction of the pressure pulse/shock wave apparatus having no focusing reflector or other focusing element. The generated waves emanate from the apparatus without coming into contact with any focusing elements. FIG. 3 shows, as an example, an electrode as a pressure pulse generating element producing divergent waves (28) behind the ignition point defined by a spark between the tips of the electrode (23, 24).

Figure 4A:
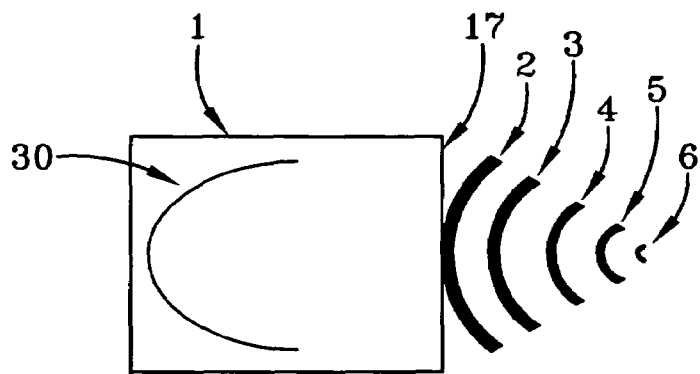
FIG. 4a is a simplified depiction of a pressure pulse/shock wave generator having a focusing element in the form of an ellipsoid. The waves generated are focused.

FIG. 4a is a simplified depiction of the pressure pulse/ shock wave generator (shock wave head) having as focusing element an ellipsoid (30). Thus, the generated waves are focused at (6).

Figure 4B:
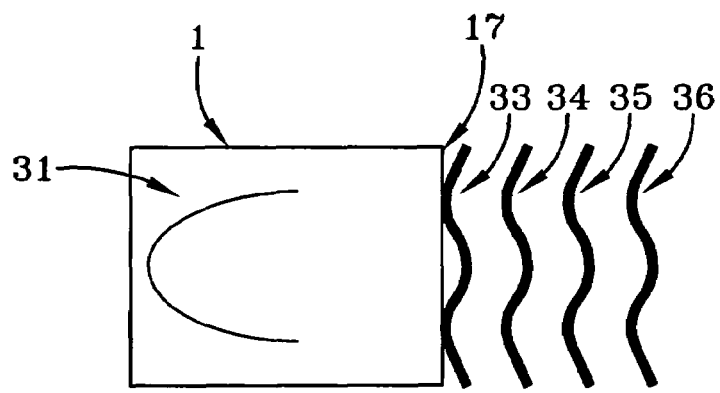
FIG. 4b is a simplified depiction of a pressure pulse/shock wave generator having a parabolic reflector element and generating waves that are disturbed plane.

FIG. 4b is a simplified depiction of the pressure pulse/ shock wave generator (shock wave head) having as a focusing element an paraboloid ($y^2=2px$). Thus, the characteristics of the wave fronts generated behind the exit window (33, 34, 35, and 36) are disturbed plane ("parallel"), the disturbance resulting from phenomena ranging from electrode burn down, spark ignition spatial variation to diffraction effects. However, other phenomena might contribute to the disturbance.

Figure 4C:
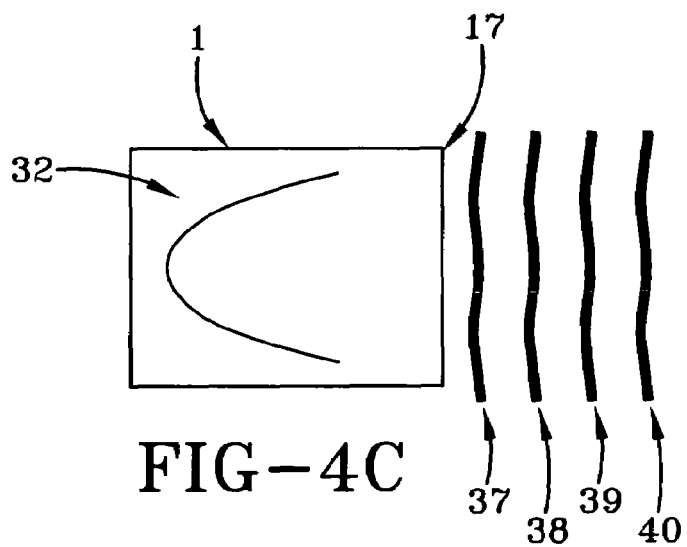
FIG. 4c is a simplified depiction of a pressure pulse/shock wave generator having a quasi parabolic reflector element (generalized paraboloid) and generating waves that are nearly plane/have nearly plane characteristics.

FIG. 4c is a simplified depiction of the pressure pulse/ shock wave generator (shock wave head) having as a focusing element a generalized paraboloid ($y^n=2px$, with $1.2<n<2.8$ and $n \neq 2$). Thus, the characteristics of the wave fronts generated behind the exit window (37, 38, 39, and 40) are, compared to the wave fronts generated by a paraboloid ($y^2=2px$), less disturbed, that is, nearly plane (or nearly parallel or nearly even (37, 38, 39, 40)). Thus, conformational adjustments of a regular paraboloid ($y^2=2px$) to produce a generalized paraboloid can compensate for disturbances from, e.g., electrode burn down. Thus, in a generalized paraboloid, the characteristics of the wave front may be nearly plane due to its ability to compensate for phenomena including, but not limited to, burn down of the tips of the electrode and/or for disturbances caused by diffraction at the aperture of the paraboloid. For example, in a regular paraboloid ($y^2=2px$) with p=1.25, introduction of a new electrode may result in p being about 1.05. If an electrode is used that adjusts itself to maintain the distance between the electrode tips ("adjustable electrode") and assuming that the electrodes burn down is 4 mm (z=4 mm), p will increase to about 1.45. To compensate for this burn down, and here the change of p, and to generate nearly plane wave fronts over the life span of an electrode, a generalized paraboloid having, for example n=1.66 or n=2.5 may be used. An adjustable electrode is, for example, disclosed in U.S. Pat. No. 6,217,531.

Figure 4D:
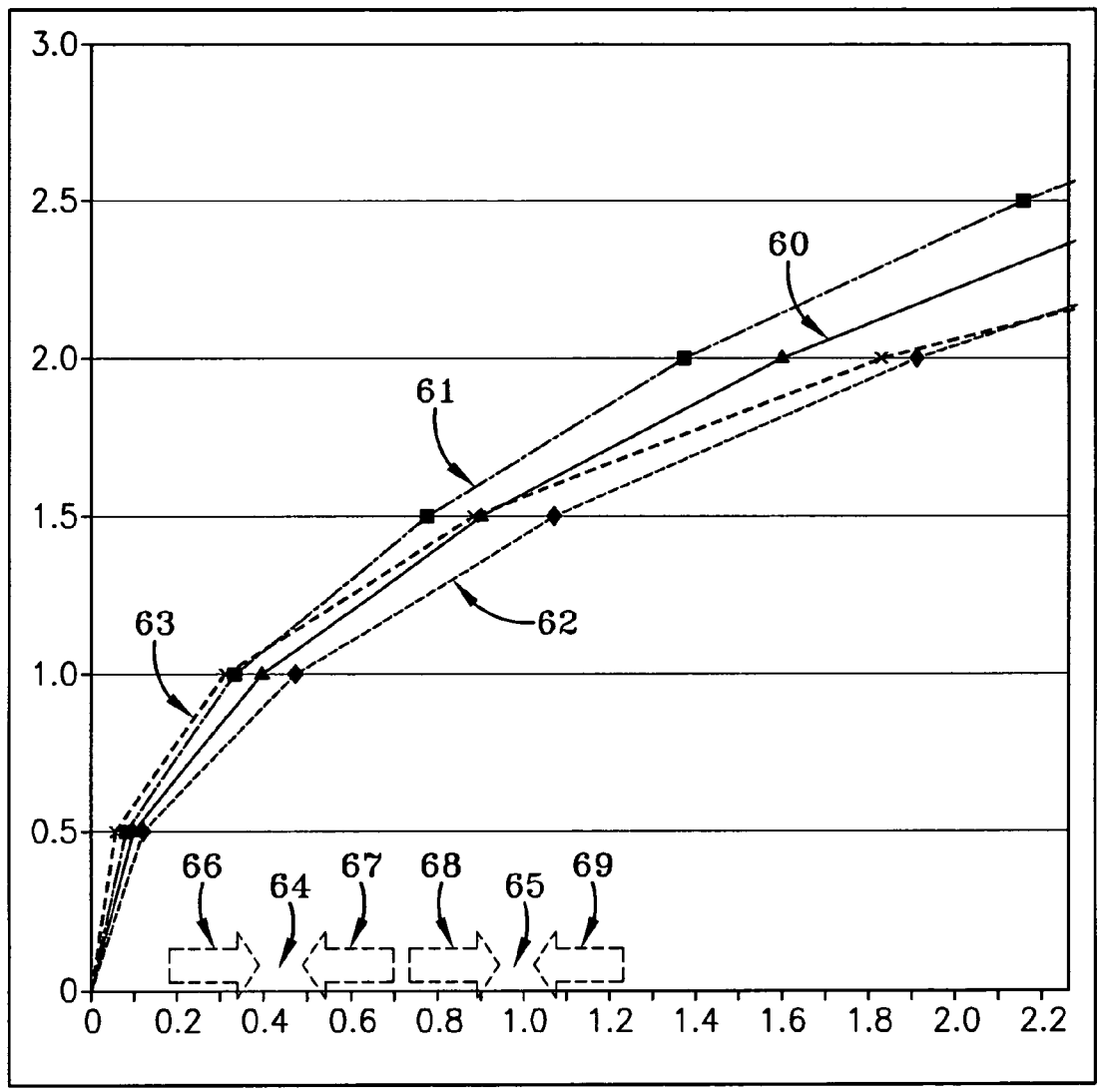
FIG. 4d is a simplified depiction of a generalized paraboloid with better focusing characteristic than a paraboloid in which n=2. The electrode usage is shown. The generalized paraboloid, which is an interpolation (optimization) between two optimized paraboloids for a new electrode and for a used (burned down) electrode is also shown.

FIG. 4d shows sectional views of a number of paraboloids. Numeral 62 indicates a paraboloid of the shape $y^2=2px$ with p=0.9 as indicated by numeral 64 at the x axis which specifies the p/2 value (focal point of the paraboloid). Two electrode tips of a new electrode 66 (inner tip) and 67 (outer tip) are also shown in the Figure. If the electrodes are fired and the tips are burning down the position of the tips change, for example, to position 68 and 69 when using an electrode which adjusts its position to compensate for the tip burn down. In order to generate pressure pulse/shock waves having nearly plane characteristics, the paraboloid has to be corrected in its p value. The p value for the burned down electrode is indicate by 65 as p/2=1. This value, which constitutes a slight exaggeration, was chosen to allow for an easier interpretation of the Figure. The corresponding paraboloid has the shape indicated by 61, which is wider than paraboloid 62 because the value of p is increased. An average paraboloid is indicated by numeral 60 in which p=1.25 cm. A generalized paraboloid is indicated by dashed line 63 and constitutes a paraboloid having a shape between paraboloids 61 and 62. This particular generalized paraboloid was generated by choosing a value of $n \neq 2$ and a p value of about 1.55 cm. The generalized paraboloid compensates for different p values that result from the electrode burn down and/or adjustment of the electrode tips.

Figure 5:
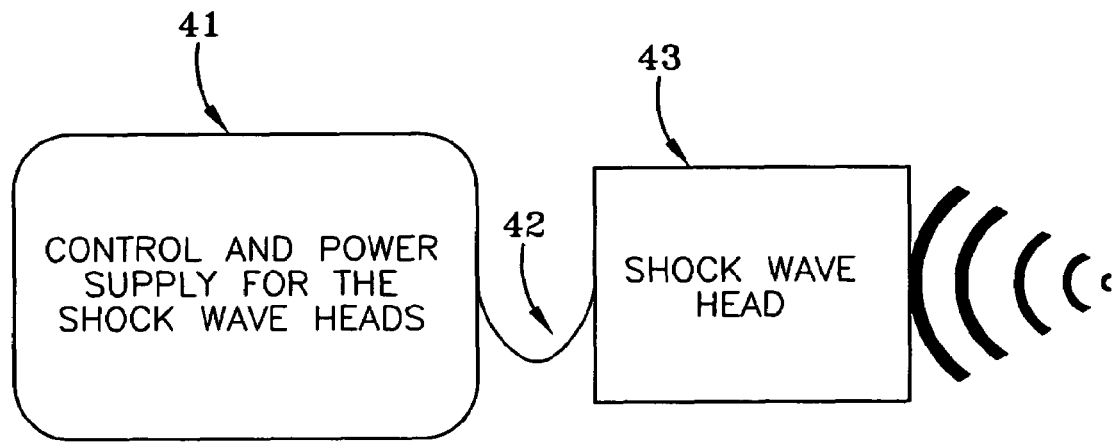
FIG. 5 is a simplified depiction of a pressure pulse/shock wave generator being connected to a control/power supply unit.

FIG. 5 is a simplified depiction of a set-up of the pressure pulse/shock wave generator (43) (shock wave head) and a control and power supply unit (41) for the shock wave head (43) connected via electrical cables (42) which may also include water hoses that can be used in the context of the present invention. However, as the person skilled in the art will appreciate, other set-ups are possible and within the scope of the present invention.

Figure 6:
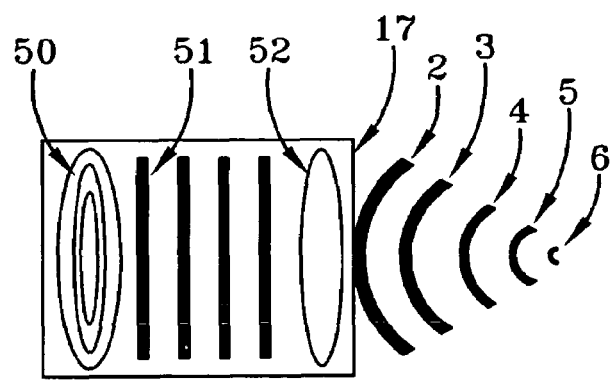
FIG. 6 is a simplified depiction of a pressure pulse/shock wave generator comprising a flat EMSE (electromagnetic shock wave emitter) coil system to generate nearly plane waves as well as an acoustic lens. Convergent wave fronts are leaving the housing via an exit window.

FIG. 6 is a simplified depiction of the pressure pulse/shock wave generator (shock wave head) having an electromagnetic flat coil 50 as the generating element. Because of the plane surface of the accelerated metal membrane of this pressure pulse/shock wave generating element, it emits nearly plane waves which are indicated by lines 51. In shock wave heads, an acoustic lens 52 is generally used to focus these waves. The shape of the lens might vary according to the sound velocity of the material it is made of. At the exit window 17 the focused waves emanate from the housing and converge towards focal point 6.

Figure 7:
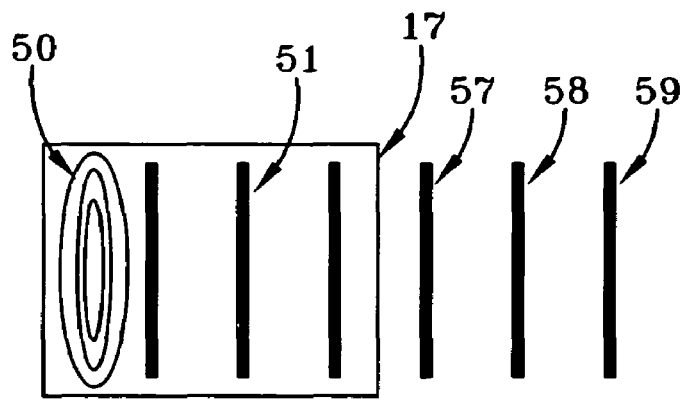
FIG. 7 is a simplified depiction of a pressure pulse/shock wave generator having a flat EMSE coil system to generate nearly plane waves. The generator has no reflecting or focusing element. As a result, the pressure pulse/shock waves are leaving the housing via the exit window unfocused having nearly plane wave characteristics.

FIG. 7 is a simplified depiction of the pressure pulse/shock wave generator (shock wave head) having an electromagnetic flat coil 50 as the generating element. Because of the plane surface of the accelerated metal membrane of this generating element, it emits nearly plane waves which are indicated by lines 51. No focusing lens or reflecting lens is used to modify the characteristics of the wave fronts of these waves, thus nearly plane waves having nearly plane characteristics are leaving the housing at exit window 17.

Figure 8:
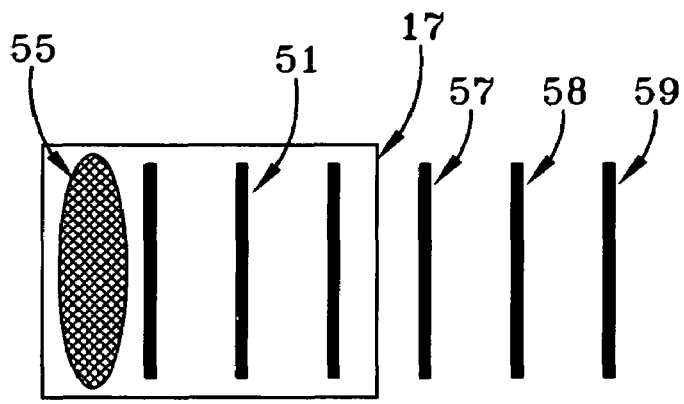
FIG. 8 is a simplified depiction of a pressure pulse/shock wave generator having a flat piezoceramic plate equipped with a single or numerous individual piezoceramic elements to generate plane waves without a reflecting or focusing element. As a result, the pressure pulse/shock waves are leaving the housing via the exit window unfocused having nearly plane wave characteristics.

FIG. 8 is a simplified depiction of the pressure pulse/shock wave generator (shock wave head) having an piezoceramic flat surface with piezo crystals 55 as the generating element. Because of the plane surface of this generating element, it emits nearly plane waves which are indicated by lines 51. No focusing lens or reflecting lens is used to modify the characteristics of the wave fronts of these waves, thus nearly plane waves are leaving the housing at exit window 17. Emitting surfaces having other shapes might be used, in particular curved emitting surfaces such as those shown in FIGS. 4a to 4c as well as spherical surfaces. To generate waves having nearly plane or divergent characteristics, additional reflecting elements or lenses might be used. The crystals might, alternatively, be stimulated via an electronic control circuit at different times, so that waves having plane or divergent wave characteristics can be formed even without additional reflecting elements or lenses.

Figure 9:
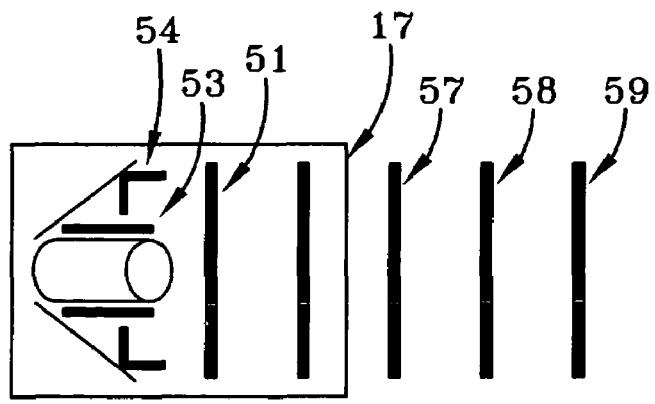
FIG. 9 is a simplified depiction of a pressure pulse/shock wave generator having a cylindrical EMSE system and a triangular shaped reflecting element to generate plane waves. As a result, the pressure pulse/shock waves are leaving the housing via the exit window unfocused having nearly plane wave characteristics.

FIG. 9 is a simplified depiction of the pressure pulse/shock wave generator (shock wave head) comprising a cylindrical electromagnet as a generating element 53 and a first reflector having a triangular shape to generate nearly plane waves 54 and 51. Other shapes of the reflector or additional lenses might be used to generate divergent waves as well.

Figure 10:
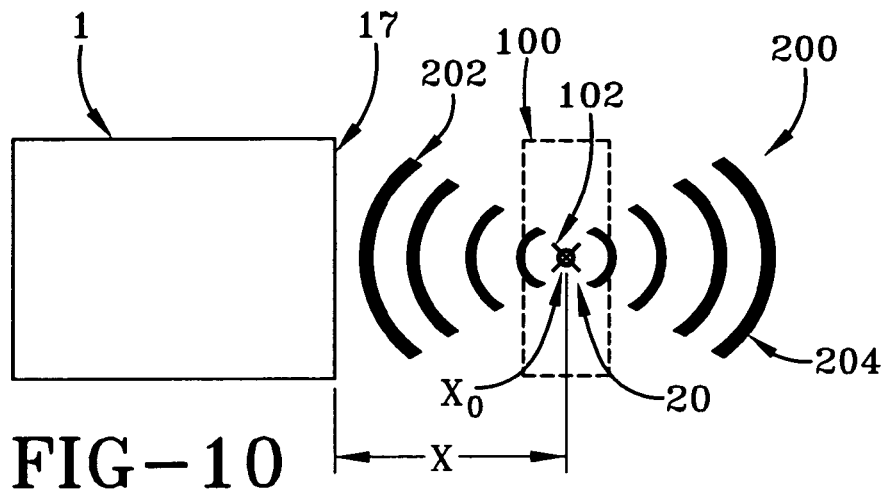
FIG. 10 is a simplified depiction of a pressure pulse/shock wave (PP/SW) generator with focusing wave characteristics shown focused with the focal point or geometrical focal volume being on an organ, the focus being targeted on the location $X_0$.
Figure 11:
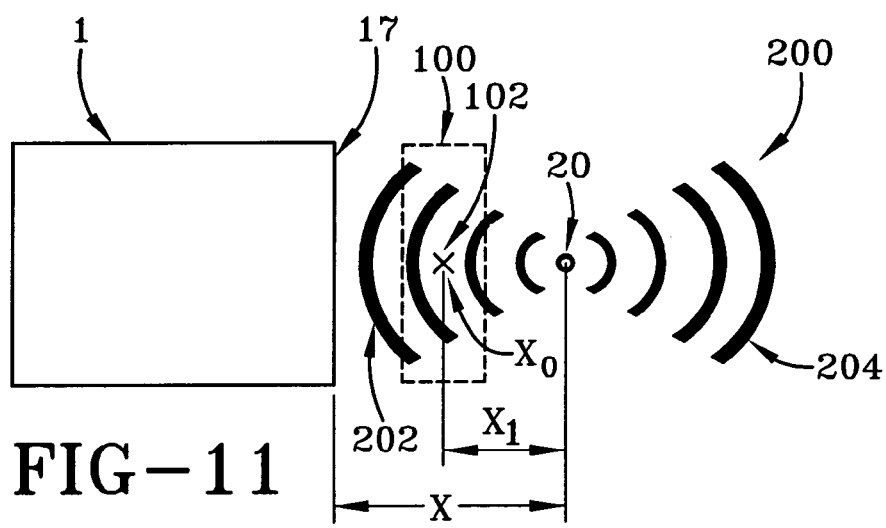
FIG. 11 is a simplified depiction of a pressure pulse/shock wave (PP/SW) generator with the focusing wave characteristics shown wherein the focus is located a distance $X_1$ from the location $X_0$ of an organ wherein the converging waves impinge the organ.
Figure 12:
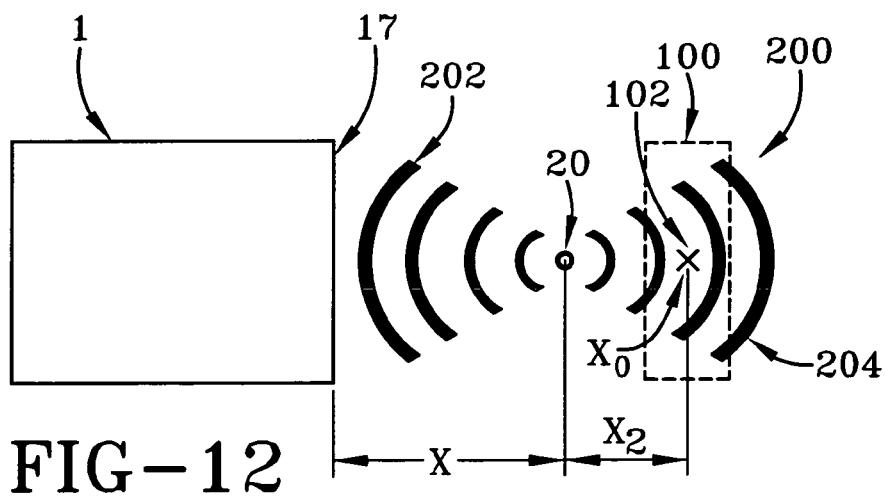
FIG. 12 is a simplified depiction of a pressure pulse/shock wave (PP/SW) generator with focusing wave characteristics shown wherein the focus is located a distance $X_2$ from the mass location $X_0$ wherein the emitted divergent waves impinge the organ.

With reference to FIGS. 10, 11 and 12 a schematic view of a shock wave generator or source 1 is shown emitting a shock wave front 200 from an exit window 17. The shock wave front 200 has converging waves 202 extending to a focal point or focal geometric volume 20 at a location spaced a distance X from the generator or source 1. Thereafter the wave front 200 passes from the focal point or geometric volume 20 in a diverging wave pattern as has been discussed in the various other FIGS. 1-9 generally.

With particular reference to FIG. 10 a tissue 100 is shown generally centered on the focal point or volume 20 at a location $X_0$ within the tissue 100. In this orientation the emitted waves are focused and thus are emitting a high intensity acoustic energy at the location $X_0$. This location $X_0$ can be anywhere within or on the organ. Assuming the tissue 100 is a gum tissue having a periodontal biofilm mass 102 at location $X_0$ then the focus is located directly on the biofilm mass 102. In one method of treating a biofilm infection or mass 102 these focused waves can be directed to destroy or otherwise reduce the biofilm mass 102 by weakening the outer barrier shield of the biofilm mass 102.

With reference to FIG. 1, the tissue 100 is shifted a distance X toward the generator or source 1. The tissue 100 at location $X_0$ being positioned a distance $X-X_1$ from the source 1. This insures the tissue 100 is impinged by converging waves 202 but removed from the focal point 20. When the tissue 100 is tissue this bombardment of converging waves 202 stimulates the cells activating the desired healing response as previously discussed.

With reference to FIG. 12, the tissue 100 is shown shifted or located in the diverging wave portion 204 of the wave front 200. As shown $X_0$ is now at a distance $X_2$ from the focal point or geometric volume 20 located at a distance X from the source 1. Accordingly $X_0$ is located a distance $X+X_2$ from the source 1. As in FIG. 10 this region of diverging waves 204 can be used to stimulate the tissue 100 which when the tissue is a cellular tissue stimulates the cells to produce the desired healing effect or response.

Heretofore invasive techniques were not used in combination with shock wave therapy primarily because the shock waves were believed to be able to sufficiently pass through interfering body tissue to achieve the desired result in a non-invasive fashion. While this may be true, in many cases if the degenerative process is such that an operation is required then the combination of an operation in conjunction with shock wave therapy only enhances the therapeutic values and the healing process of the patient and the infected organ such that regenerative conditions can be achieved that would include not only revascularization of gums, but also the heart or other organs wherein sufficient or insufficient blood flow is occurring but also to enhance the improvement of ischemic tissue that may be occupying a portion of the infected tissue or organ. This ischemic tissue can then be minimized by the regenerative process of using shock wave therapy in the fashion described above to permit the tissue to rebuild itself in the region that has been afflicted.

As shown in FIGS. 1-12 the use of these various acoustic shock wave forms can be used separately or in combination to achieve the desired therapeutic effect of destroying the periodontal biofilm mass 102.

Furthermore such acoustic shock wave forms can be used in combination with drugs, chemical treatments, irradiation therapy or even physical therapy and when so combined the stimulated cells will more rapidly assist the body's natural healing response and thus overcomes the otherwise potentially tissue damaging effects of these complimentary procedures.

The present invention provides an apparatus for an effective treatment of indications, which benefit from high or low energy pressure pulse/shock waves having focused or unfocused, nearly plane, convergent or even divergent characteristics. With an unfocused wave having nearly plane, plane, convergent wave characteristic or even divergent wave characteristics, the energy density of the wave may be or may be adjusted to be so low that side effects including pain are very minor or even do not exist at all.

In certain embodiments, the apparatus of the present invention is able to produce waves having energy density values that are below $0.1$ mJ/mm2 or even as low as $0.000\ 001$ mJ/mm2. In a preferred embodiment, those low end values range between $0.1$-$0.001$ mJ/mm2. With these low energy densities, side effects are reduced and the dose application is much more uniform. Additionally, the possibility of harming surface tissue is reduced when using an apparatus of the present invention that generates unfocused waves having planar, nearly plane, convergent or divergent characteristics and larger transmission areas compared to apparatuses using a focused shock wave source that need to be moved around to cover the affected area. The apparatus of the present invention also may allow the user to make more precise energy density adjustments than an apparatus generating only focused shock waves, which is generally limited in terms of lowering the energy output. Nevertheless in some cases the first use of a high energy focused shock wave targeting the biomass may be the best approach to weaken the outer barrier of the shield of the biomass followed by a transmission of lower energy unfocused wave patterns, the combination being the most effective in germicidal destruction of the periodontal biofilm mass.

The treatment of the above mentioned tissue, organ or body of a patient is believed to be a first time use of acoustic shock wave therapy in the preventive pre-exposure or post-exposure to periodontal biofilm infections. None of the work done to date has treated the above mentioned biofilm infections with convergent, divergent, planar or near-planar acoustic unfocused shock waves of low energy or high energy focused shock waves in a germicidal transmission path from the emitting source lens or cover to the infection. Also this is believed to be a first time use of acoustic shock waves for germicidal wound cleaning or preventive medical treatments for such exposures.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

The use of acoustic shock waves to patients exposed to biofilm infections stimulates a cellular response of the treated tissues as well as a cellular response in the surrounding tissue. This response activates otherwise dormant cells to increase the body's own defense mechanisms, allowing the cells to limit the migration of the infection and resultant tissue damage, but also to initiate the healing process. This feature means that the treating physician has the added benefit of a patient whose body will be strengthened to mitigate damage to otherwise healthy tissues and organs.

The nature of infectious disease treatments employing only antibiotics to kill infections is well known to actually make biofilm protected microorganisms mutate making them even harder to kill. The result is the patient is in a greatly weakened state overall. These mutant strains are so severe that the common antibiotic treatments are losing their ability to stop the spread of some infections which is well documented. These symptoms are generally reversible. The more serious complications may not be reversible. In some cases gum damage and complete destruction of the teeth has been observed as a consequence of such failed treatments. These antibiotic treatments can be cumulative in their adverse reactions and thus the effective treatment of the infections can also permanently damage otherwise healthy tissue and organs. The use of the shock waves as described above stimulates these healthy cells to defend against this spill over intrusion.

This means the physician can use these antibiotic treatments with far less adverse reactions if he combines the treatments with one or more exposures to acoustic shock waves either before introducing chemical antibiotic agents or shortly thereafter or both. This further means that the patient's recovery time should be greatly reduced because the patient treated with shock waves will have initiated a healing response that is much more aggressive than heretofore achieved without the cellular stimulation provided by pressure pulse or shock wave treatments. The current use of medications to stimulate such cellular activity is limited to absorption through the bloodstream via the blood vessels. Acoustic shock waves stimulate all the cells in the region treated activating an almost immediate cellular release of infection fighting and healing agents. Furthermore, as the use of other wise conflicting chemicals is avoided, adverse side effects can be limited to those medicaments used to destroy the infectious cells. In other words the present invention is far more complimentary to such antibiotic treatments in that the stimulation of otherwise healthy cells will greatly limit the adverse and irreversible effects on the surrounding non-infected tissues and organs.

A further benefit of the use of acoustic shock waves is there are no known adverse indications when combined with the use of other medications or drugs. In fact the activation of the cells exposed to shock wave treatments only enhances cellular absorption of such medication making these drugs faster acting than when compared to non stimulated cells. As a result, it is envisioned that the use of one or more medicaments prior to, during or after subjecting the patient to acoustic shock waves will be complimentary to the treatment or pre-conditioning treatment for periodontal biofilm exposures. It is further appreciated that certain drug therapies can be altered or modified to lower risk or adverse side effects when combined with a treatment involving acoustic shock waves as described above.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. The method of treatment for a periodontal tissue at risk for exhibiting a periodontal disease or periodontal condition in a diagnosed patient comprises the steps of:
receiving the diagnosed patient;
activating an acoustic shock wave or pressure pulse generator or source to emit pressure pulses or acoustic shock waves directed toward the periodontal tissue to impinge the periodontal tissue with shock waves or pressure pulses having a low energy density in the range of 0.00001 mJ/mm$^2$ to 1.0 mJ/mm$^2$, the pressure pulse being an acoustic pulse which includes several cycles of positive and negative pressure, wherein the pressure pulse has an amplitude of the positive part of such a cycle should be above 0.1 MPa and the time duration of the pressure pulse is from below a microsecond to about a second, rise times of the positive part of the first pressure cycle in the range of nano-seconds (ns) up to some milli-seconds (ms), the acoustic shock waves being very fast pressure pulses having amplitudes above 0.1 MPa and rise times of the amplitude being below 100's of ns, the duration of the shock wave is typically below 1-3 micro-seconds ($\mu$s) for the positive part of a cycle and typically above some micro-seconds for the negative part of a cycle; and
subjecting the periodontal tissue, or the entire periodontal region of the patient to convergent, divergent, planar or near planar acoustic shock waves or pressure pulses stimulating said tissue, wherein the tissue is positioned within a path of the emitted shock waves or pressure pulses and away from any localized geometric focal volume or point of the emitted shock waves or pressure pulses wherein the emitted shock waves or pressure pulses either have no geometric focal volume or point or have a focal volume or point ahead of the periodontal tissue or beyond the periodontal tissue thereby passing the emitted waves or pulses through the periodontal tissue while avoiding having any localized focal point within the periodontal tissue wherein the emitted pressure pulses or shock waves are convergent, divergent planar or near planar and the pressure pulse shock wave generator or source is based on electro-hydraulic, electromagnetic, piezoceramic or ballistic wave generation having an energy density value ranging as low as 0.00001 mJ/mm$^2$ to a high end of below 1.0 mJ/mm$^2$.

2. The method of treatment of claim 1 wherein the emitted shock waves or pressure pulses are convergent having one or more geometric focal volumes of points at a distance of at least X from the generator or source, the method further comprising positioning the periodontal tissue at a distance at or less than the distance X from the source.

3. The method of treatment of claim 1 further comprises the step of:
administering one or more medicaments prior, during or after subjecting the patient to acoustic shock waves or pressure pulses.

4. The method of treatment of claim 1 further comprises the step of:
testing the bacterial count or viability of the treated tissue or region of the diagnosed patient after exposure to one or more acoustic shock wave or pressure pulse treatments.

5. The method of treatment of claim 1 further comprises the step of:
subjecting the periodontal tissue to a surgical procedure to remove or repair some or all of any defects or degenerative tissues.

6. The method of treatment of claim 1 wherein the treated periodontal tissue has an indication of one or more pathological conditions including:
a periodontal biofilm mass, periapical endodontic lesions, endo-perio lesions, gingivitis, inflammation of gingival tissue, periodontitis, progressive loss of ligament, cementum or alveolar bone support to teeth.

7. The method of claim 1 wherein the treated tissue has one or more conditions requiring treatment as follows:
ridge augmentation for cosmetic, prosthetic or implantation of teeth; to assist osteoblastic and osteoclastic processes in orthodontia; regeneration of alveolar bone surrounding loose teeth implants regeneration of structures supporting the teeth including regeneration of structures supporting teeth including gingival, periodontal ligament, cementum and alveolar bone.

8. The method of claim 1 wherein the treatment is for prevention of periodontal disease.

9. The method of claim 8 further comprises the step of: debridement.

10. The method of claim 8 wherein the treatment further comprises the step of:
destroying biofilm in or on the treated tissue or region.

11. The method of claim 8 wherein the treated tissue or region activates or otherwise stimulates stem cells or release of cellular growth factors in the oral structure effecting a tissue repair or tissue regeneration.

12. The method of treatment for a periodontal tissue at risk of or exhibiting a periodontal disease or periodontal condition in a diagnosed patient comprises the steps of:
receiving the diagnosed patient;

activating an acoustic shock wave or pressure pulse generator or source to emit pressure pulses or acoustic shock waves directed toward the periodontal tissue to impinge the periodontal tissue with shock waves having a low energy density in the range of 0.00001 mJ/mm$^2$ to 1.0 mJ/mm$^2$, the pressure pulse being an acoustic pulse which includes several cycles of positive and negative pressure, wherein the pressure pulse has an amplitude of the positive part of such a cycle should be above 0.1 MPa and the time duration of the pressure pulse is from below a microsecond to about a second, rise times of the positive part of the first pressure cycle in the range of nano-seconds (ns) up to some milli-seconds (ms), the acoustic shock waves being very fast pressure pulses having amplitudes above 0.1 MPa and rise times of the amplitude being below 100's of ns, the duration of the shock wave is typically below 1-3 micro-seconds (μs) for the positive part of a cycle and typically above some micro-seconds for the negative part of a cycle;

subjecting the periodontal tissue, or the entire periodontal region of the patient to convergent, divergent, planar or near planar acoustic shock waves or pressure pulses stimulating said tissue in the absence of creating cavitation bubbles in the treated periodontal tissue, wherein the tissue is positioned within a path of the emitted shock waves or pressure pulses and away from any localized geometric focal volume or point of the emitted shock waves or pressure pulses wherein the emitted shock waves or pressure pulses either have no geometric focal volume or point or have a focal volume or point ahead of the periodontal tissue or beyond the periodontal tissue thereby passing the emitted waves or pulses through the periodontal tissue while avoiding having any localized focal point within the periodontal tissue wherein the emitted pressure pulses or shock waves are convergent, divergent planar or near planar and the pressure pulse shock wave generator or source is based on electrohydraulic, electromagnetic, piezoceramic or ballistic wave generation having an energy density value ranging as low as 0.00001 mJ/mm$^2$ to a high end of below 1.0 mJ/mm$^2$; and wherein the periodontal tissue has cells and the shock waves or pressure pulses stimulate a cellular response in the tissue in the absence of cellular damage in the tissue caused by the shock waves or pressure pulses evidenced by the avoidance of localized hemorrhaging as a result of exposure to the emitted shock waves or pressure pulses.

13. The method of treatment of claim 12 wherein the tissue is gums.

14. The method of treatment of claim 12 wherein the step of subjecting the periodontal tissue to acoustic shock waves or pressure pulses stimulates at least some of said cells within said periodontal tissue to release or produce one or more of nitric oxygen (NO), vessel endothelial growth factor (VEGF), bone morphogenetic protein (BMP) or other growth factors.

15. The method of treatment of claim 12 further comprises the step of:
administering one or more medicaments prior, during or after subjecting the patient to acoustic shock waves or pressure pulses.

16. The method of treatment of claim 12 further comprises the step of:
testing the bacterial count or viability of the treated tissue or region of the diagnosed patient after exposure to one or more acoustic shock wave or pressure pulse treatments.

17. The method of treatment of claim 12 further comprises the step of:
subjecting the periodontal tissue to a surgical procedure to remove or repair some or all of any defects or degenerative tissues.

18. The method of treatment of claim 12 wherein the treated periodontal tissue has an indication of one or more pathological conditions including:
a periodontal biofilm mass, periapical endodontic lesions, endo-perio lesions, gingivitis, inflammation of gingival tissue, periodontitis, progressive loss of ligament, cementum or alveolar bone support to teeth.

19. The method of claim 12 wherein the treated tissue has one or more conditions requiring treatment as follows:
ridge augmentation for cosmetic, prosthetic or implantation of teeth; to assist osteoblastic and osteoclastic processes in orthodontia; regeneration of alveolar bone surrounding loose teeth implants regeneration of structures supporting the teeth including regeneration of structures supporting teeth including gingival, periodontal ligament, cementum and alveolar bone.

20. The method of claim 12 wherein the treatment is for prevention of periodontal disease.

21. The method of claim 12 further comprises the step of: debridement.

22. The method of claim 12 wherein the treatment further comprises the step of:
destroying biofilm in or on the treated tissue or region.

23. The method of claim 12 wherein the treated tissue or region activates or otherwise stimulates stem cells or release of cellular growth factors in the oral structure effecting a tissue repair or tissue regeneration.

* * * * *